(12) United States Patent
Moon et al.

(10) Patent No.: US 9,238,633 B2
(45) Date of Patent: *Jan. 19, 2016

(54) METHODS FOR TREATING DIABETIC COMPLICATIONS WITH CARBAMOYLOXY ARYLALKANOYL ARYLPIPERAZINE COMPOUNDS

(71) Applicant: SK BIOPHARMACEUTICALS CO., LTD., Seoul (KR)

(72) Inventors: Hong Sik Moon, Daejeon (KR); Han Ju Yi, Daejeon (KR); Eun Hee Chae, Daejeon (KR); Sang Mi Chae, Daejeon (KR); Hye Won Shin, Daejeon (KR)

(73) Assignee: SK BIOPHARMACEUTICALS CO., LTD., Seoul (KR)

( * ) Notice: Subject to any disclaimer, the term of this patent is extended or adjusted under 35 U.S.C. 154(b) by 78 days.

This patent is subject to a terminal disclaimer.

(21) Appl. No.: 14/163,836

(22) Filed: Jan. 24, 2014

(65) Prior Publication Data

US 2014/0243352 A1    Aug. 28, 2014

Related U.S. Application Data

(63) Continuation of application No. 13/805,098, filed as application No. PCT/KR2011/004996 on Jul. 8, 2011, now Pat. No. 8,648,083.

(30) Foreign Application Priority Data

Jul. 8, 2010    (KR) .......................... 10-2010-0065950

(51) Int. Cl.
*C07D 295/192*  (2006.01)
*A61K 31/495*  (2006.01)
(Continued)

(52) U.S. Cl.
CPC .......... *C07D 295/192* (2013.01); *A61K 9/2054* (2013.01); *A61K 31/495* (2013.01); *A61K 31/496* (2013.01); *C07D 317/66* (2013.01)

(58) Field of Classification Search
CPC ............. C07D 295/192; C07D 317/66; A61K 9/2054; A61K 31/495; A61K 31/496
See application file for complete search history.

(56) References Cited

U.S. PATENT DOCUMENTS

| 6,906,094 B2 | 6/2005 | Barvian et al. ........ A61K 31/404 |
| 2009/0181967 A1 | 7/2009 | Boyd et al. ................. 514/235.8 |
| 2013/0131081 A1 | 5/2013 | Moon et al. ..................... 31/495 |

FOREIGN PATENT DOCUMENTS

| JP | 2004-503534 | 2/2004 |
| KR | 10-2008-0067364 | 7/2008 |

(Continued)

OTHER PUBLICATIONS

International Diabetes Federation (http://www.idf.org/complications-diabetes, accessed May 29, 2015).*

(Continued)

*Primary Examiner* — Savitha Rao
*Assistant Examiner* — Angela Brown-Pettigrew
(74) *Attorney, Agent, or Firm* — Harness, Dickey & Pierce, P.L.C.

(57) ABSTRACT

A method of treating diabetic complications with carbamoyloxy arylalkanoyl arylpiperazine compounds including:

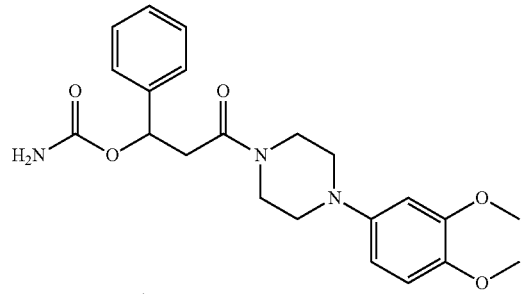

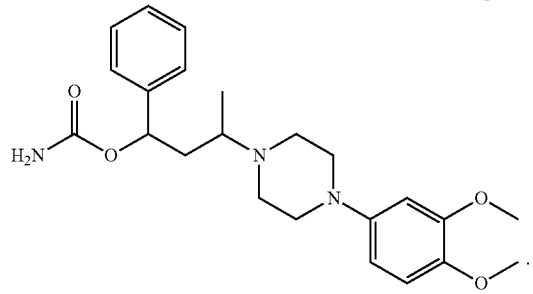

10 Claims, 3 Drawing Sheets

(51) Int. Cl.
  A61K 31/496 (2006.01)
  A61K 9/20 (2006.01)
  C07D 317/66 (2006.01)

(56) References Cited

FOREIGN PATENT DOCUMENTS

| | | |
|---|---|---|
| KR | 10-2008-0100765 | 11/2008 |
| WO | WO 2007/051982 | 5/2007 |
| WO | WO 2008/140197 | 11/2008 |
| WO | WO 2008/140198 | 11/2008 |

OTHER PUBLICATIONS

Claesson, H.E. (2009). "On the biosynthesis and biological role of eoxins and 15-lipooxygenase-1 in airway inflammation and Hodgkin lymphoma." *Prostaglandins and Other Lipid Mediators.* 89:120-125.

Dwarakanath, R. et al. (2008). "Viral vector-mediated 12/15-lipoxygenase overexpression in vascular smooth muscle cells enhances inflammatory gene expression and migration." *Journal of Vascular Research.* 45:132-142.

Hajek, A. et al. (2008). "12/15-Lipoxygenase deficiency protects mice from allergic airways inflammation and increases secretory IgA levels." *J Allergy Clin Immunol.* 122:633-639.e3.

Harats, et al., (2000) "Overexpression of 15-Lipoxygenase in Vascular Endothelium Accelerates Early Atherosclerosis in LDL Receptor—Deficient Mice", *Arteriosclerosis, Thrombosis & Vascular Biology*, vol. 20, No. 9, pp. 2100-2105.

Hatley, M. et al. (2003). "Increased production of 12/15 lipoxygenase eicosanoids accelerates monocyte/endothelial interactions in diabetic db/db mice." *The Journal of Biological Chemistry.* 278(28):25369-25375.

Jeon, S.G. et al. (2009). "15-lipoxygenase metabolites play an important role in the development of a T-helper type 1 allergic inflammation induced by double-stranded RNA." *Clinical & Experimental Allergy.* 39:908-917.

Liu, C. et al. (2009). "15-lipoxygenase-1 induces expression and release of chemokines in cultured human lung epithelial cells." *American Journal of Physiology—Lung Cellular and Molecular Physiology.* 297:L196-L203.

Ma, J. et al. (2005). "12/15-Lipoxygenase inhibitors in diabetic nephropathy in the rat." *Elsevier Ltd: Prostaglandins, Leukotrienes and Essential Fatty Acids.* 72:(1):13-20.

Montero, A. et al. (2000). "15-lipoxygenase in glomerular inflammation." *Experimental Nephrology.* 8:14-19.

Nagelin, et al., (2009) "Murine 12/15-Lipoxygenase Regulates ATP-binding Cassette Transporter G1 Protein Degradation through p38- and JNK2-dpendent Pathways", *J Bol. Chem.* vol. 284(45):31303-31314.

Natarajan, et al., (2004) "ATVB in Focus, Diabetic Vascular Disease: Pathophysiological Mechanisms in the Diabetic Milieu and Therapeutic Implications", *Arteriosclerosis, Thrombosis & Vascular Biology*, vol. 24, No. 9, pp. 1542-1548.

Natarajan, R. et al. (2003). "Lipoxygenases and lipid signaling in vascular cells in diabetes." *Frontiers in Bioscience.* 8:s783-795.

Obrosova, I. et al. (2006). "Role for 12/15-lipoxygenase in diabetic neuropathy." *Diabetes* 55(Suppl.1). AI88(801-P).

Reilly, K. et al. (2004). "12/15-Lipoxygenase activity mediates inflammatory monocyte/endothelial interactions and atherosclerosis in vivo." *The Journal of Biological Chemistry.* 279(10):9440-9450.

Shannon, V. et al. (1993). "Histochemical evidence for induction of arachidonate 15-lipoxygenase in airway disease." *American Review of Respiratory Disease.* 147:1024-1028.

Siu, D. (2010). "A new way of targeting to treat coronary artery disease." *Journal of Cardiovascular Medicine (Hagerstown).* 11(1):1-6.

Xu, Z.G. et al. (2006). "Relationship between 12/15-lipoxygenase and COX-2 in mesangial cells: potential role in diabetic nephropathy." *Kidney International.* 69:512-519.

Xu, Z.G. et al. (2009). "Angiotensin II type 1 receptor expression is increased via 12-lipoxygenase in high glucose-stimulated glomerular cells and type 2 diabetic glomeruli." *Nephrology Dialysis Transplantation.* 24(6):1744-1752.

Yuan, H. et al. (2008). "Effects of cholesterol-tagged small interfering RNAs targeting 12/15-lipoxygenase on parameters of diabetic nephropathy in a mouse model of type 1 diabetes." *American Journal of Physiology—Renal Physiology.* 295(2):F605-617.

Supplemental European Search Report dated Dec. 6, 2013 in European Application No. EP 11803822.3.

International Search Report for Application No. PCT/KR2011/004996 dated Feb. 10, 2012 (5 pgs.).

Office Action dated May 24, 2013 in U.S. Appl. No. 13/805,098.

Williams and Nadler (2007) "Inflammatory Mechanisms of Diabetic Complications." *Curr. Diabetes Rep.* 7:242-48.

Törnblom et al. (2005) "Non-infected preterm parturition is related to increased concentrations of IL-6, IL-8 and MCP-I in human cervix." *Reproduct. Biol. & Endocrinol.* 3:39.

Chae, et al., (2012). "Synthesis and pharmacological evaluation of carbamic acid 1-phenyl-3-(4-phenyl-piperazine-1-yl)-propyl ester derivatives as new analgesic agents". *Biorganic & Medical Chemistry Letters* 22:2434-2439.

V.I. Pokrovskij, "Encyclopedicheskij slovar', 2-e isdanie", *M., Medicina*, pp. 167-168, with English citation of relevant Part D1, (2015).

Belikov (1993). *V.G. Pharmacevticheskaja khimija. M., Vysschaja shkola*, pp. 43-47 with English citation of relevant Part D2.

\* cited by examiner

METHODS FOR TREATING DIABETIC COMPLICATIONS WITH CARBAMOYLOXY ARYLALKANOYL ARYLPIPERAZINE COMPOUNDS

CROSS-REFERENCE TO RELATED APPLICATIONS

This application is a continuation application of U.S. application Ser. No. 13/805,098, filed on Dec. 18, 2012, which claims the benefit and priority to PCT/KR2011/004996, filed Jul. 8, 2011. The entire disclosures of the applications identified in this paragraph are incorporated herein by references.

TECHNICAL FIELD

This application claims the benefit of Korean Patent Application No. 10-2010-0065950, filed on Jul. 8, 2010, in the Korean Intellectual Property Office, the disclosure of which is incorporated herein in its entirety by reference.

The present invention relates to a pharmaceutical composition including a carbamoyloxy arylalkanoyl arylpiperazine compound and a method of treating a disease selected from the group consisting of diabetic nephropathy, diabetic neuropathy, diabetic vascular complications, hyperlipidemia, coronary artery disease, and inflammation by using the pharmaceutical composition.

BACKGROUND ART

Lipoxygenases are non-heme iron-containing enzymes that are found in plants and animals and catalyze the oxygenation of particular polyunsaturated fatty acids, such as lipids and lipoproteins. Several different lipoxygenases having particular oxidation reactions are known. Lipoxygenases of a mammal are named according to where they are located in arachidonate that is to be oxygenated. Three types of lipoxygenase of a human are known, and they catalyze addition of oxygen molecules to carbon sites 5, 12 and 15 of arachidonate. Accordingly, the enzymes are named as 5-, 12- or 15-lipoxygenase according to location of a carbon site to which oxygen molecules are added. 5-lipoxygenase converts arachidonate into 5-hydroperoxyeicosatetraenate (5-HPETE). This is a first phase of a metabolism pathway for generating 5-hydroxyeicosatetraenate (5-HETE) and leukotriene (LT). Likewise, 12- and 15-lipoxygenases respectively convert arachidonate into 12-HPETE and 15-HPETE. Biochemical reduction of 12-HPETE induces 15-HETE, which is a precursor of compounds known as 15-HETE lipoxin. Various biological effects are related to products having a lipoxygenase activity, and many of these products are known as mediating factors for various diseases. 15-lipoxygenase is usually expressed in endothelial cells, smooth muscle cells, monocytes/macrophages, glomerulus mesangial cells, renal tubular epithelial cells, and podocytes, and catalyzes formation of 15-S-hydroxyeicosatetraenate (15-S-HETE) from rachidonate (Nataraj an and Nadler, *Front. Biosci.* (2003) 8:s783-795; Reilly et al., *J. Biol. Chem.* (2004) 279(10):9440-9450).

Diabetic chronic complications include macrovascular complications, diatbetic nephropathy, diabetic neuropathy, etc. If diabetes mellitus continues for several years, microvessels and macrovessels slowly undergo pathologic alteration. Microvascular complications develop directly due to hyperglycemia. If formation of sorbitol is facilitated by hyperglycemia, a thickness of blood vessel walls is increased and blood flow is affected, thereby facilitating blood coagulation. If micro vessel lesions induced by continual hyperglycemia occur in kidney, neurons, etc., diabetic chronic complications, such as diabetic nephropathy diabetic neuropathy, may develop. Meanwhile, hyperglycemia is an indirect cause of macrovascular complications, and an increase in cholesterol due to abnormal lipid metabolism in a hyperglycemia state is a direct cause of hyperglycemia.

Prior art discloses that 15-lipoxygenase is involved in the development of arteriosclerosis, glomerulonephritis, hyperlipidemia, or inflammation. Also, KR 2008-67364 discloses triazole compounds as 15-lipoxygenase inhibitors. However, an agent for preventing or treating such diseases by inhibiting 15-lipoxygenase is not yet commercially available. Thus, there is a need to develop a pharmaceutical composition for preventing or treating such diseases.

DISCLOSURE OF INVENTION

Technical Problem

The present invention provides a pharmaceutical composition for preventing or treating a disease selected from the group consisting of diabetic nephropathy, diabetic neuropathy, diabetic vascular complications, hyperlipidemia, coronary artery disease, and inflammation.

The present invention also provides a method of treating a disease selected from the group consisting of diabetic nephropathy, diabetic neuropathy, diabetic vascular complications, hyperlipidemia, coronary artery disease, and inflammation by using the pharmaceutical composition.

Solution to Problem

According to an aspect of the present invention, there is provided a pharmaceutical composition for preventing or treating a disease selected from the group consisting of diabetic nephropathy, diabetic neuropathy, diabetic vascular complications, hyperlipidemia, coronary artery disease, and inflammation, wherein the pharmaceutical composition includes a therapeutically effective amount of a compound selected from the group consisting of a compound represented by Formula I below, a pharmaceutically acceptable salt, isomer, solvate, or hydrate thereof, and a combination thereof; and a pharmaceutically acceptable carrier:

Formula I wherein, $X_1$ comprises at least one selected from the group consisting of hydrogen, linear or branched C1-C6 alkyl, F, Cl or Br-containing halogen, linear or branched C1-C6 alkoxy, nitro, and trifluoromethyl;

$X_2$ comprises at least one selected from the group consisting of hydrogen, linear or branched C1-C6 alkyl, halogen, linear or branched C1-C6 alkoxy, nitro, trifluoromethyl, and if $X_2$ comprises two or more thereof, they are identical to or different from each other and form a cycle together with an adjacent carbon atom; and Y is hydrogen or methyl, or forms a carbonyl together with an adjacent carbon atom.

A pharmaceutical composition according to an embodiment of the present invention may include a therapeutically effective amount of a compound selected from the group consisting of a compound represented by Formula I above, a pharmaceutically acceptable salt, isomer, solvate, or hydrate thereof, and a combination thereof.

The term "treating" is interpreted as preventing development of a disease or state, suppressing a disease or state, that is, suppressing development of a disease or state, and alleviating a disease or state, that is, causing regression of a disease or state in an animal that has a disease selected from the group consisting of diabetic nephropathy, diabetic neuropathy, diabetic vascular complications, hyperlipidemia, coronary artery disease, and inflammation or a state or that has not been diagnosed as having the disease or state but is prone to have the disease or state. Accordingly, the term "therapeutically effective amount" refers to an amount that is sufficient to obtain a pharmaceutical effect, that is, a therapeutic effect.

The compound represented by Formula I according to an embodiment of the present invention may be prepared by one of ordinary skill with respect to synthesis of compounds in the art by using known compounds, or compounds that are easily prepared therefrom. In particular, preparation methods for the compound are disclosed in detail in KR 2008-40393, which is also filed by the identical inventors of the present invention, and the patent is incorporated herein by reference. Compounds of the present invention may be chemically synthesized by using methods disclosed in the cited reference above. However, the methods are used for illustrative purposes only. Accordingly, a process sequence used therein may be optionally altered if needed, and may not limit the scope of the present invention.

The compound may further include, in addition to the compound represented by Formula I, a pharmaceutically acceptable salt thereof, that is, an acid or base additional salt thereof, and a stereochemical isomer of the compound represented by Formula I herein the pharmaceutically acceptable salt may be any one of various salts that allow a parent compound to maintain its activity in a subject that is to be administered with the compound and that do not cause adverse effects. The pharmaceutically acceptable salt may be an inorganic salt or an organic salt. Examples of an acid are an acetic acid, a hydrochloric acid, a nitric acid, an aspartic acid, a sulfonic acid, a sulfuric acid, a maleic acid, a glutamic acid, a formic acid, a succinic acid, a phosphoric acid, phthalic acid, a tannic acid, a tartaric acid, a hydrobromic acid, a propionic acid, a benzene sulfonic acid, a benzoic acid, a staric acid, a esylic acid, a butryc acid, a bicarbonic acid, a biculfuric acid, a bitartaric acid, an oxalic acid, a butylic acid, a calcium edetic acid, a camsylic acid, a carbonic acid, a chlorobenzoic acid, a citric acid, an idetic acid, a toluene sulfonic acid, an edicylinic acid, an ecylinic acid, a fumaric acid, a gluceptic acid, a pamoic acid, a gluconic acid, a glycolyllarsanylic acid, a methylnitric acid, a polygalatronic acid, a hexyllisorcynonic acid, a maloic acid, a hydrobamic acid, a hydrochlorinic acid, a hydroiodoic acid, a hydroxylnaphtholic acid, an icethionic acid, a lactobionic acid, a mandelic acid, an estolinic acid, a mucic acid, a naphcylic acid, a muconic acid, a p-nitromethansulfonic acid, a hexamic acid, a pantotenic acid, a monohydrogenphosphoric acid, a dihydrogenphosphoric acid, a salicylic acid, a sulpamic acid, a sulpanylic acid, a methanesulfonic acid, and a theoclic acid.

For example, the acid for an additional salt may be a hydrochloric acid or a methansulfonic acid. Also, examples of a basic salt are an ammonium salt, and a salt of an alkali or alkali earth metal, such as lithium, sodium, potassium, magnesium, or calcium. Detailed examples of the basic salt are a salt containing an organic base, such as a benzathine, N-methyl-D-glucamine, or hydrabamine salt, and a salt containing an amino acid, such as arginine or lysine. Also, the salts may be converted into a free radical form by treatment with an appropriate base or acid. The term "additional salt" includes a solvent compound that is formed from the compound represented by Formula I and a salt thereof. Examples of the solvent compound are hydrates and alcoholates.

Also, the stereochemical isomer of the compound represented by Formula I according to an embodiment of the present invention refers to any compound that is obtainable from the compound represented by Formula I. If not defined otherwise, chemical appellations of compounds indicate any possible stereochemical isomer type mixtures, and examples of the mixture are diastereomers and enantiomers each having a basic molecular structure. In particular, a stereocenter may have a R- or S-coordination, and a substituent of 2-valent cyclic (partially) saturated radical may have cis- or trans-coordination. A compound having a double bond may have E or Z-stereochemistry in the double bond. The stereochemical isomer of the compound represented by Formula I is induced to be included in the scope of the present invention.

Non-limiting examples of the compound represented by Formula I are carbamic acid 3-[4-(3,4-dimethoxy-phenyl)-piperazine-1-yl]-3-oxo-1-phenyl-propyl ester, carbamic acid 3-[4-(3,4-dimethoxy-phenyl)-piperazine-1-yl]-1-(4-fluoro-phenyl)-3-oxo-propyl ester, carbamic acid 3-(4-benzo[1,3]dioxol-5-yl-piperazine-1-yl)-3-oxo-1-phenyl-propyl ester, carbamic acid 3-[4-(3,4-dimethoxy-phenyl)-piperazine-1-yl]-1-(4-trifluoromethyl-phenyl)-3-oxo-propyl ester;hydrochloride, carbamic acid 3-[4-(3,4-dimethoxy-phenyl)-piperazine-1-yl]-1-(4-nitro-phenyl)-3-oxo-propyl ester, (R)-carbamic acid 3-[4-(4-chloro-phenyl)-piperazine-1-yl]-3-oxo-1-phenyl-propyl ester, (S)-carbamic acid 3-[4-(3,4-dimethoxy-phenyl)-piperazine-1-yl]-3-oxo-1-phenyl-propyl ester, (R)-carbamic acid 3-[4-(3,4-dimethoxy-phenyl)-piperazine-1-yl]-3-oxo-1-phenyl-propyl ester, carbamic acid 3-[4-(3,4-dimethoxy-phenyl)-piperazine-1-yl]-1-phenyl-butyl ester, and carbamic acid 3-[4-(3,4-dimethoxy-phenyl)-piperazine-1-yl]-1-(4-chloro-phenyl)-3-oxo-propyl ester. According to an embodiment of the present invention, the compound represented by Formula I may be (R)-carbamic acid 3-[4-(3,4-dimethoxy-phenyl)-piperazine-1-yl]-3-oxo-1-phenyl-propyl ester.

The pharmaceutical composition according to an embodiment of the present invention may include a pharmaceutically acceptable carrier.

The pharmaceutically acceptable carrier of the pharmaceutical composition may be any one of various materials that are conventionally used in formulations, and non-limiting examples of the pharmaceutically acceptable carrier are lactose, dextrose, sucrose, sorbitol, mannitol, starch, acacia rubber, calcium phosphate, alginate, gelatin, calcium silicate, microcrystal cellulose, polyvinylpyrrolidone, cellulose, water, syrup, methyl cellulose, methylhydroxybenzoate, propylhydroxybenzoate, talc, magnesium stearate, and mineral oil. The pharmaceutical composition may further include a lubricant, a wetting agent, a flavoring agent, an emulsifier, a suspension agent, a preservative, etc. Suitable pharmaceutically acceptable carriers and formulations are disclosed in detail in *Remington's Pharmaceutical Sciences*(19th ed., 1995).

According to an embodiment of the present invention, the pharmaceutical composition may be orally or parenterally administered. The parental administration may be intravenous infusion, subcutaneous infusion, intramuscular infusion, intraperitoneal infusion, endothelium administration, topical administration, intranasal administration, intra-vaginal administration, intrapulmonary administration, or intrarectal administration. In the case of oral administration, an active material may be coated, or formulated to be protected from decomposition in a stomach. Also, the pharmaceutical composition may be administered via any device that allows an active material to reach a target cell. An administration pathway may differ according to a general condition and age of a to-be-treated subject, a property of a treatment condition, and an active material used.

A suitable administration amount of the pharmaceutical composition may differ according to a formation method, an administration method, an age, weight, sex, and morbid state of a patient, food, an administration time, an administration pathway, an excretion rate, and reaction sensitivity. Typically, skilled physicians may determine and prescribe an administration amount that is effective for treatment or prevention without any difficulty. The administration amount of the pharmaceutical composition may be given all at once, or may be divided into several portions, and for example, the pharmaceutical composition may be administered one to four times per day.

The pharmaceutical composition may be formulated in a unit dosage form by using a method that is obvious to one of ordinary kill in the art and a pharmaceutically acceptable carrier and/or an excipient, or may be prepared by using a multi-dosage container. In this case, the formulation may be a solution, suspension, or emulsion in an oil or aqueous medium, an extract, powder, granule, tablet, or capsule, and a dispersant or a stabilizer may be further included in the pharmaceutical composition. Also, the pharmaceutical composition may be administrated in the formulation of a suppository, spray, ointment, cream, gel, inhalant, or dermal patch.

The pharmaceutical composition may be used to prevent or treat diabetic nephropathy, diabetic neuropathy or diabetic vascular complications.

The term "diabetic" means that a cause of a corresponding disease is diabetes. Also, the term "diabetes" refers to a disease group that is characterized as chronic hyperglycemia induced by deficient insulin operation and that has various abnormal metabolisms due to chronic hyperglycemia. Accordingly, the diabetic nephropathy, diabetic neuropathy, and diabetic vascular complications are respectively understood as nephropathy induced by diabetes, neuropathy induced by diabetes, and vascular complications induced by diabetes.

Diabetic nephropathy refers to a disease in which microvessels of the kidney are impaired and thus, proteins are directly discharged without filtration. Diabetic nephropathy develops due to glomerulus hiperpenentration, novel glomerulus basement membrane thickening, glomerular mesangium cell proliferation, glomerulus thickening, and synthesis and increase of extracellular matrix, and causes gradual glomerulosclerosis and renal failure. Diabetic neuropathy is a nervous system complication of diabetes in which an abnormality occurs in a function or structure of neurons due to diabetes, and often develops in a peripheral nerve system. Also, diabetic vascular complications refer to a disease in which angiosclerosis develops due to diabetes-induced hyperglycemia and metabolic disorder, such as, insulin resistance, resulting in blood flow disorder.

Also, the pharmaceutical composition is used to prevent or treat hyperlipidemia, coronary artery disease, or inflammation.

Hyperlipidemia refers to a state in which metabolism of fat, such as triglycerides or cholesterol, is abnormally performed and thus, blood contains a great amount of fat, and when a fatty material is present in blood, it may accumulate on blood vessel walls, causing inflammation, and thus causing cardiovascular disease. Also, the coronary artery disease refers to a state in which fatty deposits and fibrous tissues accumulate in an artery (coronary artery or heart artery) through which blood is supplied to the heart, and thus, blood supply to cardiac muscle is reduced so that angina pectoris, myocardial necrosis, and myocardial infarction develop and thus, functions of the heart are seriously impaired. According to an embodiment of the present invention, a cause of the hyperlipidemia or coronary artery disease may or may not be diabetes.

Inflammation is understood by one of ordinary skill in the art as including a symptom that is characterized as a topical or systemic defense response, and may be caused by chemical and/or physiological reactions against physical external wounds, infection, the chronic diseases as described above, and/or external stimuli (for example, part of an allergic reaction). The reactions cause destruction, delusion, or isolation of wound tissues. For example, inflammation develops due to pyrexia, tumescence, pain, flare, vasodiation, and/or increased blood flow, invasion of white blood into infected sites, or loss of function and/or inflammatory state related other symptoms. Accordingly, inflammation is understood as including an inflammatory disease, disorder, or state, and in particular, acute, chronic, ulcerative, specific, allergic, and necrotic inflammation, and other types of inflammation known to one of ordinary skill in the art. Accordingly, the pharmaceutical composition may be used in treating asthma, chronic obstructive pulmonary (COPD), pulmonary fibrosis, allergic disease, rhinitis, inflammatory bowel disease, ulcer, inflammatory pain, pyrexia, arteriosclerosis, coronary artery disease, vasculitis, pancretitis, arthritis, osteoarthritis, rheumatoid arthritis, conjuctivitis, iritis, scleritis, uveitis, wound healing, dermatitis, eczema, psoriasis, stroke, diabetes, autoimmune disease, Alzheimer's disease, multiple sclerosis, sarcoidosis, Hodgkin disease, other malignancies, and other types of diseases having an inflammatory factor.

According to an embodiment of the present invention, the compound may have an inhibitory activity of 15-lipoxygenase.

It is known that 15-lipoxygenase relates to a cause of various diseases including arteriosclerosis, asthma, glomerulonephritis, diabetic chronic complication, etc. (Harats et al., *Arterioscler. Thromb. Vasc. Biol.*, (2000) 20(9):2100-2105; Natarajan et al., *Front Biosci.*, (2003)8:s783-795; Hatley et al., *J. Biol. Chem.*, (2003)278(28):25369-25375; Shannon et al., *Am. Rev. Respir. Dis.*, (1993)147(4):1024-1028; Montero and Badr, *Exp. Neph.*, (2000)8(1):14-19; Hatley et al., *J. Biol. Chem.*, (2003)278(28): 25369-25375; Natarajan et al., *Arterioscler Thromb. Vasc. Biol.,* 24, (2004)24(9):1542-1548; Ma et al., *Prostaglandins Leukot Essent Fatty Acids.*, (2005)72(1):13-20; Xu et al., *Kidney Int.*, (2006)69(3):512-9; Dwarakanath et al., *J. Vasc. Res.*, (2008)45(2):132-142), and expression of 15-lipoxygenase is enhanced in a diabetes state or a hyperglycemia state. The enhanced expression of 15-lipoxygenase affects various metabolisms, signaling network, transcription control, and gene expression, thereby increasing formation of free radicals, lipid peroxidation, mitogenactivated protein (MAP) kinase, and inflammatory reactions. Such results contribute to the development of diabetic complications, and by artificially inhibiting expression or activity of 15-lipoxygenase, diabetic vascular complications, diabetic nephropathy, and diabetic neuropathy are preventable and treatable in a diabetes animal model (Natarajan and Nadler, *Front. Biosci.* (2003)8:s783-795; Reilly et al., *J. Biol. Chem.* (2004)279(10):9440-9450; Obrosova et al., *Diabetes* 55(Supp1.1)(2006)A188; Xu et al., *Nephrol Dial Transplant.*, (2009)24(6):1744-1752; Yuan et al., *Am J Physiol Renal Physiol.* (2008)295(2):F605-617). Also, inhibiting expression or activity of 15-lipoxygenase is suggested as a method of preventing or treating coronary artery disease that is or is not induced by diabetes (Siu, *J Cardiovasc Med* (Hagerstown), (2010) 11(1):1-6; Nagelin et al., *J. Biol. Chem.* (2009) 284(45):31303-31314; Natarajan et al., *Front Biosci.* (2003) 8:s783-95; Hatley et al., *J. Biol. Chem.* (2003) 278 (28):25369-25375), and also, since 15-lipoxygenase plays an important role in biosynthesis of asthma, allergy, psoriasis, and since inflammation mediating factors and an inhibitor of the enzyme inhibits a biochemical pathway related to the disease states, inhibition of 15-lipoxygenase is useful in treating the inflammation-related diseases (Liu et al., *Am J Physiol Lung Cell Mol Physiol.* (2009) 297(1):1196-1203; Jeon et al., *Clin Exp Allergy.* (2009) 39(6):908-917; Claesson, *Prostaglandins Other Lipid Mediat.* (2009) 89(3-4):120-125; Hajek, *J Allergy Clin Immunol.*, (2008) 122(3):633-639).

Accordingly, a compound exhibiting the inhibitory activity against 15-lipoxygenase may be used as an agent for preventing or treating the diabetic nephropathy, diabetic neuropathy, diabetic vascular complications, hyperlipidemia, coronary artery disease, or inflammation as described above.

Another aspect of the present invention provides a method of treating a disease selected from the group consisting of diabetic nephropathy, diabetic neuropathy, diabetic vascular complications, hyperlipidemia, coronary artery disease, and inflammation, wherein the method includes contacting the pharmaceutical composition and a subject.

The contacting may be performed in vitro or in vivo. If the contacting is performed in vivo, the method may further include administrating the pharmaceutical composition to the subject.

The subject may be a cell, a tissue, an organ, or an individual. Also, the administration may involve directly contacting a solution of the pharmaceutical composition dissolved in an appropriate buffer solution and a cell, a tissue, or an organ, or may be parental administration. The pharmaceutical composition and administration method used in the treatment have already been described above and thus will not be described in detail herein.

Meanwhile, the subject to which the pharmaceutical composition is administrable may be any kind of animal. For example, the subject may be a human, or a non-human animal, such as a dog, a cat, or a mouse.

BRIEF DESCRIPTION OF DRAWINGS

The above and other features and advantages of the present invention will become more apparent by describing in detail exemplary embodiments thereof with reference to the attached drawings in which.

MODE FOR THE INVENTION

The present invention will be described in further detail with reference to the following examples. These examples are for illustrative purposes only and are not intended to limit the scope of the present invention.

EXAMPLE 1

Synthesis of carbamic acid 3-[4-(3,4-dimethoxy-phenyl)-piperazine-1-yl]-3-oxo-1-phenyl-propyl ester

554 mg (2.887 mmole) of ethyl benzoylacetate and 641 mg (2.887 mmole) of 3,4-dimethoxyphenylpiperazine were dissolved in toluene and refluxed for 24 hours. 736 mg (1.99 mmole) of a compound obtained after concentration under reduced pressure was dissolved in methanol and cooled to a temperature of 0° C., and 109 mg (2.887 mmole) of sodium borohydride was slowly added thereto. The resultant solution was stirred for 2 hours at room temperature, and then a solvent was concentrated under reduced pressure and diluted with water and extracted several times with ethyl acetate. Then, an obtained organic layer was dried using magnesium sulfate and filtered and concentrated under reduced pressure. The obtained residue was refined by column chromatography (hexane: ethylacetate=1:1), thereby obtaining 1.592 mmole (589 mg) of a compound. The obtained compound was dissolved in tetrahydrofurane (10 mL), and then 820 mg (5 mmole) of 1,1'-carbomidiazol was added thereto and stirred at room temperature for 1 hour, and excess ammonia water was added thereto and stirred at room temperature for 1 hour. The reaction mixture was diluted with water, and extracted several times with ethyl acetate and an obtained organic layer was dried with magnesium sulfate and filtered and concentrated under reduced pressure. The obtained residue was refined by column chromatography (ethyl acetate) to produce a target compound (Amount: 329 mg, Yield: 28%).

$^1$H NMR(200 MHz, CDCl3) d: 2.82(dd, 1H), 3.04(m, 5H), 3.61(m, 2H), 3.77(m, 2H), 3.88(d, 6H), 4.77(br, 2H), 6.15(t, 1H), 6.42(d, 1H), 6.57(s, 1H), 6.82(d, 1H), 7.41(m, 5H)

EXAMPLE 2

Synthesis of carbamic acid 3-[4-(3,4-dimethoxy-phenyl)-piperazine-1-yl]-1-(4-fluoro-phenyl)-3-oxo-propyl ester A target compound was obtained in the same manner as in Example 1, except that 4-fluoro-benzoylacetate and 3,4-dimethoxyphenylpiperazine were used as starting materials (Amount: 542 mg, Yield: 37%).

$^1$H NMR(200 MHz, CDCl3) d: 2.82(dd, 1H), 3.01(m, 5H), 3.60(m, 2H), 3.75(m, 2H), 3.86(d, 6H), 4.92(br, 2H), 6.15(t, 1H), 6.42(d, 1H), 6.56(d, 1H), 6.80(d, 1H), 7.04(t, 2H), 7.38(t, 2H)

EXAMPLE 3

Synthesis of carbamic acid 3-(4-benzo[1,3]dioxol-5-yl-piperazine-1-yl)-3-oxo-1-phenyl-propyl ester A target compound was obtained in the same manner as in Example 1, except that ethyl benzoylacetate and 3,4-methylenedioxyphenylpiperazine were used as starting materials (Amount: 190 mg, Yield: 48%)

$^1$H NMR(200 MHz, CDCl3) d: 2.98(m, 6H), 3.59(m, 2H), 3.76(m, 2H), 4.71(br, 2H), 5.94(s, 2H), 6.15(t, 1H), 6.36(dd, 1H), 6.55(s, 1H), 6.74(d, 1H), 3.40(m, 5H)

EXAMPLE 4

Synthesis of carbamic acid 3-[4-(3,4-dimethoxy-phenyl)-piperazine-1-yl]-1-(4-trifluoromethyl-phenyl)-3-oxo-propyl ester;hydrochloride A target compound was obtained in the same manner as in Example 1, except that ethyl-4-trifluoromethyl-benzoylacetate and 3,4-dimethoxy phenylpiperazine were used as starting materials (Amount: 250 mg, Yield: 52%). A generated product was dissolved in dichloromethane and a saturated HCl/ether solution was added thereto to produce hydrochloride.

$^1$H NMR(200 MHz, DMSO) d: 2.90(dd, 1H), 3.12(dd, 1H), 3.34(m, 4H), 3.75(s, 3H), 3.78(s, 3H), 3.85(m, 4H), 6.00(m, 1H), 6.60(br, 2H), 7.01(m, 2H), 7.20(m, 1H), 7.60(d, 2H), 7.75(d, 2H)

EXAMPLE 5

Synthesis of carbamic acid 3-[4-(3,4-dimethoxy-phenyl)-piperazine-1-yl]-1-(4-nitro-phenyl)-3-oxo-propyl ester A target compound was obtained in the same manner as in Example 1, except that ethyl-4-nitro-benzoylacetate and 3,4-dimethoxy phenylpiperazine were used as starting materials (Amount: 261 mg, Yield: 57%).

$^1$H NMR(200 MHz, DMSO) d: 2.96(dd, 1H), 3.16(dd, 1H), 3.42(m, 4H), 3.76(s, 3H), 3.78(s, 3H), 3.92(m, 4H), 6.05(m, 1H), 6.64(br, 2H), 7.02(m, 1H), 7.24(m, 2H), 7.65(d, 2H), 8.24(d, 2H)

EXAMPLE 6

Synthesis of (R)-carbamic acid 3-[4-(4-chloro-phenyl)-piperazine-1-yl]-3-oxo-1-phenyl-propyl ester 1.0 g (6.0 mmole) of (R)-3-hydroxy-3-phenylpropionic acid and 1.18 g (6.0 mmole) of 4-chloro phenylpiperazine were dissolved in 50 mL of tetrahydrofurane as a solvent at room temperature, and 1.24 g (6.0 mmole) of EDC and 0.81 g (6 mmole) of HOBt were dropped thereinto and stirred at a temperature of 25° C. for 5 hours. Excess solvent was removed therefrom by distillation under reduced pressure, and the resultant product was neutralized with 20 mL of 1 N aqueous sodium chloride solution, and 25 mL of ethyl acetate was added thereto and an obtained organic layer was isolated and extracted twice with 15 mL of ethyl acetate. The organic layer was dried with 2 g of anhydrous magnesium sulfate and filtered, and a filtrate was concentrated under reduced pressure and isolation-purified by column chromatograph (hexane:ethyl acetate=1:1 to 1:10). 0.345 g (1 mmole) of an obtained product was dissolved in 15 mL of tetrahydrofurane and then 0.325 g (2 mmole) of 1,1'-carbodimidazole was added thereto and stirred for 1 hour at room temperature, and then, an excess ammonia solution was added thereto and stirred for 2 hours at room temperature. A reaction mixture was diluted with water and extracted several times with ethyl acetate, and an obtained organic layer was dried with magnesium sulfate, and concentrated under reduced pressure. An obtained residue was purified by column chromatography (hexane:ethyl acetate=1:1), thereby producing a target compound (Amount: 1.2 g, Yield: 52.5%).

$^1$H NMR(200 MHz, CDCl3) d: 2.82(dd, 1H), 3.07(m, 5H), 3.58(m, 2H), 3.74(m, 2H), 4.81(br, 2H), 6.13(t, 1H), 6.84(d, 2H), 7.38(m, 7H)

EXAMPLE 7

Synthesis of (S)-carbamic acid 3-[4-(3,4-dimethoxyphenyl)-piperazine-1-yl]-3-oxo-1-phenyl-propylester A target compound was obtained in the same manner as in Example 6, except that (S)-3-hydroxy-3-phenylpropionic acid (6 mmole) and 3,4-dimethoxy phenylpiperazine (6 mmole) were used as starting materials (Amount: 1.38 g, Yield: 56%)

$^1$H NMR(200 MHz, CDCl3) d: 2.82(dd, 1H), 3.04(m, 5H), 3.61(m, 2H), 3.77(m, 2H), 3.88(d, 6H), 4.77(br, 2H), 6.15(t, 1H), 6.42(d, 1H), 6.57(s, 1H), 6.82(d, 1H), 7.41(m, 5H)

EXAMPLE 8

Synthesis of (R)-carbamic acid 3-[4-(3,4-dimethoxyphenyl)-piperazine-1-yl]-3-oxo-1-phenyl-propylester A target compound was obtained in the same manner as in Example 6, except that (R)-3-hydroxy-3-phenylpropionic acid and 3,4-dimethoxy phenylpiperazine were used as starting materials (Amount: 1.040 g, Yield: 42%)

$^1$H NMR(200 MHz, CDCl3) d: 2.82(dd, 1H), 3.04(m, 5H), 3.61(m, 2H), 3.77(m, 2H), 3.88(d, 6H), 4.77(br, 2H), 6.15(t, 1H),

EXAMPLE 9

Synthesis of carbamic acid 3-[4-(3,4-dimethoxyphenyl)-piperazine-1-yl]-1-phenyl-butyl ester

Phenyl-1-prophenyl-ketone (4.1 mmole) and 3,4-dimethoxy phenylpiperazine (4.9 mmole) were dissolved in 30 mL of ethanol as a solvent and stirred at a temperature of 72° C. for 48 hours. The solvent was distilled under reduced pressure, and the resultant mixture was diluted with water, extracted twice with water, and extracted twice with ethylacetate. An organic layer was distilled under reduced pressure, and then, dried with magnesium sulfate and filtered, and a filtrate was concentrated under reduced pressure and purified by column chromatography (hexane: ethylacetate=4:1), thereby producing a compound. The compound (2.9 mmole)

was dissolved in 20 mL of methanol and NaBH$_4$(3.8 mmole) was slowly added thereto. The resultant product was stirred at room temperature for 2 hours, a solvent was concentrated under reduced pressure, and a yellow residue was purified by column chromatography (hexane: ethylacetate=1:1). The purified compound (2 mmole) was dissolved in 15 ml of tetrahydrofurane and then 1,1'-carbodiimidazole (4 mmole) was added thereto and stirred at room temperature for 1 hour, and excess ammonia water was added thereto and stirred for 2 hours at room temperature. A reaction mixture was diluted with water and extracted several times with ethyl acetate, and an obtained organic layer was dried with magnesium sulfate and concentrated under reduced pressure. An obtained residue was purified by column chromatography (hexane:ethyl acetate=1:1), thereby producing a final product (Amount: 90.9 mg, Yield: 22%).

$^1$H NMR (200 MHz, CDCl3) d 1.81(m, 1H), 2.32(m, 1H), 2.5(m, 3H), 2.8(m, 2H), 3.14(m, 4H), 3.80(s, 6H), 4.80(br, 2H), 6.02(t, 1H), 6.92(m, 4H), 7.36(m, 5H)

EXAMPLE 10

Synthesis of carbamic acid 3-[4-(3,4-dimethoxy-phenyl)-piperazine-1-yl]-1-(4-chloro-phenyl)-3-oxo-propyl ester A target compound was obtained in the same manner as in Example 1, except that ethyl-4-chloro-benzoylacetate and 3,4-dimethoxyphenylpiperazine were used as starting materials (Amount: 543 mg, Yield: 42%).

$^1$H NMR(200 MHz, CDCl3) d: 2.82(dd, 1H), 3.01(m, 5H), 3.61(m, 2H), 3.77(m, 2H), 3.86(d, 6H), 4.84(br, 2H), 6.15(t, 1H), 6.42(d, 1H), 6.57(s, 1H), 6.82(d, 1H), 7.35(s, 4H)

EXAMPLE 11

In-vitro test on inhibitory effect on 15-lipoxygenase

In order to confirm that the compounds manufactured according to Examples 1 to 10 specifically inhibit only 15-lipoxygenase, human platelet-induced 12-lipoxygenase as a negative control and rabbit reticulocyte cells-induced 15-lipoxygenase as a test group were used to identify an inhibitory effect of the compounds on 12-lipoxygenase.

12-lipoxygenase reacts with arachidonate as a substrate to produce 12-hydroxyeicosatetrenoate (12-HETE) as a product. Accordingly, 12-lipoxygenase activity is evaluated by measuring an amount of generated 12-HETE by spectrometry. Also, 15-lipoxygenase reacts with a linolenic acid as a substrate to produce 13-hydroperoxy-9,11-octadecadienoic acid (13-HPODE) as a product. Accordingly, 15-lipoxygenase activity is evaluated by measuring an amount of generated 13-HPODE by spectrometry.

12-lipoxygenase activity was measured when a concentration of each of the compounds was 10 µM. Each sample was pretreated by using a buffer solution (50 mM Tris-HCl, 0.1% Triton X-100, pH 7.4) at a temperature of 25° C. for 15 minutes and then, 30 µM arachidonate (a concentration thereof was controlled to be 30 µM during reaction) was added thereto and reacted at a temperature of 25° C. for 15 minutes, and an amount of 12-HETE as a generated product was measured by absorbance at a wavelength of 570 nm.

15-lipoxygenase activity was measured when a concentration of each of the compounds was 10 µM. Each sample was pretreated by using a buffer solution buffer solution (phosphate buffered saline buffer, pH 7.4) at a temperature of 4° C. for 15 minutes, and then 260 µM linolenic acid (a concentration thereof was controlled to be 260 µM during reaction) was added and reacted at a temperature of 4° C. for 10 minutes, and an amount of 13-HPODE as a generated product was measured by absorbance at a wavelength of 660 nm.

Results obtained by measuring the inhibitory effect of the compounds on 12-lipoxygenase and 15-lipoxygenase activity are shown in Table 1.

TABLE 1

| Example | Compound | 15-lipoxygenase Inhibitory level at 10 uM (%) | 12-lipoxygenase Inhibitory level at 10 uM (%) |
|---|---|---|---|
| 1 | Carbamic acid 3-[4-(3,4-dimethoxy-phenyl)-piperazine-1-yl]-3-oxo-l-phenyl-propyl ester | 73 | 10 |
| 2 | Carbamic acid 3-[4-(3,4-dimethoxy-phenyl)-piperazine-1-yl]-1-(4-fluoro-phenyl)-3-oxo-propyl ester | 69 | −5 |
| 3 | Carbamic acid 3-(4-benzo[1,3]dioxol-5-yl-piperazine-1-yl)-3-oxo-1-phenyl-propyl ester | 85 | −8 |
| 4 | Carbamic acid 3-[4-(3,4-dimethoxy-phenyl)-piperazine-1-yl]-1-(4-trifluoromethyl-phenyl)-3-oxo-propyl ester; hydrochloride | 48 | 0 |
| 5 | Carbamic acid 3-[4-(3,4-dimethoxy-phenyl)-piperazine-1-yl]-1-(4-nitro-phenyl)-3-oxo-propyl ester | 75 | 0 |
| 6 | (R)-carbamic acid 3-[4-(4-chloro-phenyl)-piperazine-1-yl]-3-oxo-1-phenyl-propyl ester | 114 | 11 |
| 7 | (S)-carbamic acid 3-[4-(3,4-dimethoxy-phenyl)-piperazine-1-yl]-3-oxo-1-phenyl-propyl ester | 69 | 2 |
| 8 | (R)-carbamic acid 3-[4-(3,4-dimethoxy-phenyl)-piperazine-1-yl]-3-oxo-1-phenyl-propyl ester | 79 | 15 |

TABLE 1-continued

| Example | Compound | 15-lipoxygenase Inhibitory level at 10 uM (%) | 12-lipoxygenase Inhibitory level at 10 uM (%) |
|---|---|---|---|
| 9 | carbamic acid 3-[4-(3,4-dimethoxy-phenyl)-piperazine-1-yl]-1-phenyl-butyl ester | 62 | 0 |
| 10 | carbamic acid 3-[4-(3,4-dimethoxy-phenyl)-piperazine-1-yl]-1-(4-chloro-phenyl)-3-oxo-propyl ester | 72 | 7 |

EXAMPLE 12

Pharmaceutical Effect Test on Diabetic Hyperlipidemia in Diabetes Animal Model

Sprague-Dawley rats (n=21, 4 weeks, male) were used as lab models (Central Lab. Animal Inc.). Rats (n=14) having diabetes induced by intraperitoneal administration of 50 mg/kg of streptozotocin were used as a test group, and rats (n=7) intraperitoneally administered with only a solvent (100 mM citric acid buffer solution, pH 4.5) were used as a control. Typically, streptozotocin destroys beta cells of the pancreas to induce diabetes, and thus, blood sugar is increased and amounts of cholesterol and triglycerides in serum are increased. 2 days after the administration of streptozotocin, diabetes was induced in the test group. The test group was divided into two groups, and rats of one group were orally administered once a day with 200 mg/kg of (R)-carbamic acid 3-[4-(3,4-dimethoxy-phenyl)-piperazine-1-yl]-3-oxo-1-phenyl-propyl ester for four weeks. The other group was orally administered with 30% polyethylene glycol (PEG) instead of the compound.

Figure 1:
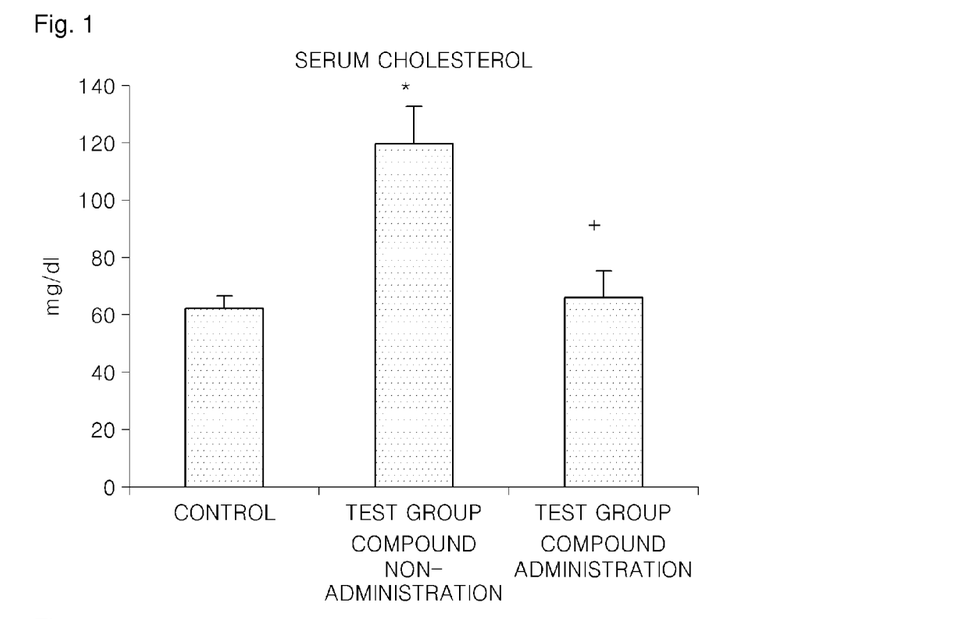
FIG. 1 shows measurement results of an amount of total cholesterol in serum obtained after a compound according to an embodiment of the present invention was administered to diabetes-induced mice.
Figure 2:
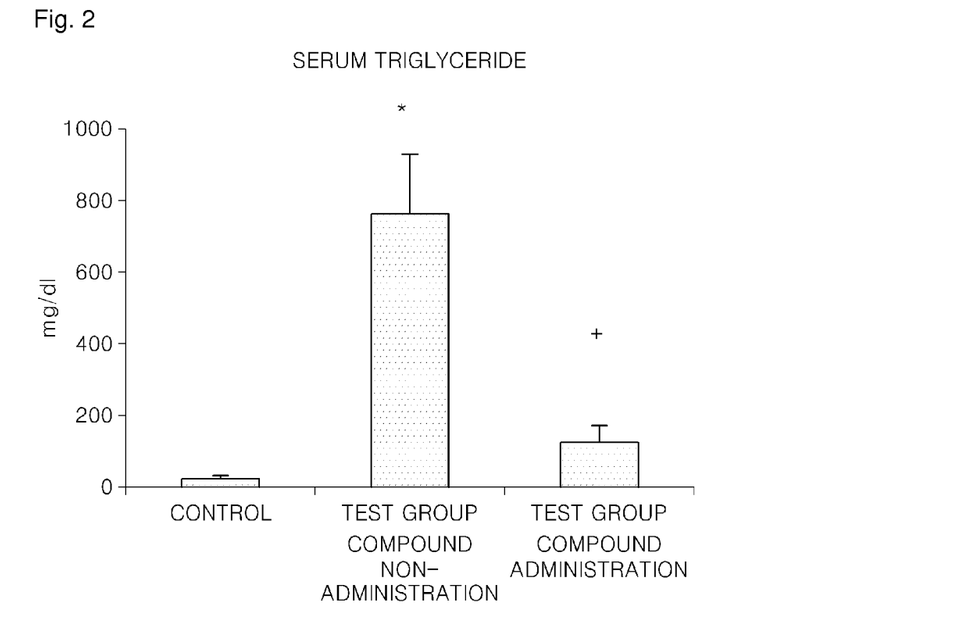
FIG. 2 shows measurement results of an amount of triglycerides in serum obtained after a compound according to an embodiment of the present invention was administered to diabetes-induced mice.

After the 4-week administration of the compound and PEG, amounts of total cholesterol and triglycerides in serum of each of the groups were measured and results thereof are shown in FIGS. 1 and 2. In order to measure the amounts of total cholesterol and triglycerides, serum was isolated from the rats and a Hitachi 7600 autoanalyzer was used. As a result, it was confirmed that due to the administration of (R)-carbamic acid 3-[4-(3,4-dimethoxy-phenyl)-piperazine-1-yl]-3-oxo-1-phenyl-propyl ester, a concentration (120±13 mg/dl) of total cholesterol increased by streptozotocin was decreased to 66±9 mg/dl similar to 62±5 mg/dl of the control, and also, a concentration (760±162 mg/dl) of triglyceride increased by streptozotocin was substantially decreased to 126±44 mg/dl. That is, the increased cholesterol and triglyceride in serum were significantly decreased due to the administration with the compound. From this result, it was confirmed that the compound is useful in preventing or treating hyperlipidemia.

EXAMPLE 13

Pharmaceutical Effect Test on Diabetic Nephropathy

Sprague-Dawley rats (n=21, 4 weeks, male) were used as lab models (Central Lab. Animal Inc.). Rats (n=14) having diabetes induced by intraperitoneal administration of 50 mg/kg of streptozotocin were used as a test group, and rats (n=7) intraperitoneally administered with only a solvent (100 mM citric acid buffer solution, pH 4.5) were used as a control. Typically, in rats having diabetes induced by streptozotocin, diabetic nephropathy is induced by hyperglycemia, and one of the symptoms is renal fibrosis, and gene expression of an extracellular matrix protein such as fibronectin is increased. 2 days after the administration of streptozotocin, diabetes was induced in the test group. The test group was divided into two groups, and rats of one group were orally administered once a day with 200 mg/kg of (R)-carbamic acid 3-[4-(3,4-dimethoxy-phenyl)-piperazine-1-yl]-3-oxo-1-phenyl-propyl ester for 4 weeks. The other group was orally administered with 30% polyethylene glycol (PEG) instead of the compound.

Figure 3:
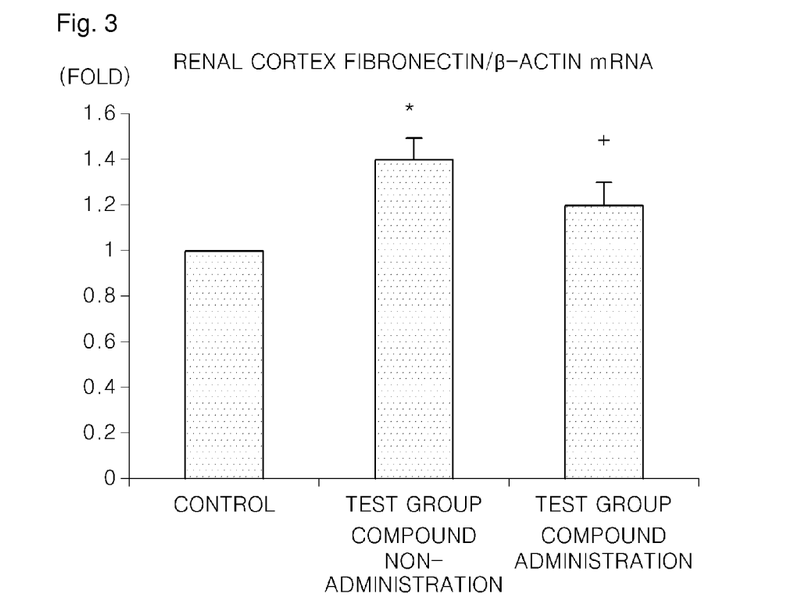
FIG. 3 shows measurement results of an expression level of fibronectin in renal cortex tissue after a compound according to an embodiment of the present invention was administered to diabetes-induced mice.

After the 4-week administration of the compound and PEG, renal cortex tissues were extracted from each of the groups and then, an expression level of fibronectin was measured by a real-time reverse transcription polymerase chain reaction (that is, an amount of mRNA transcribed from fibronectin) (see FIG. 3). The expression level of fibronectin was measured by using a forward primer (5'-GCCACAC-CTACAACCAGTAT-3'; SEQ ID NO: 1) and a reverse primer (5'-ATGACCACTCAGAAATGGAG-3'; SEQ ID NO: 2). In the RT-PCR, annealing was performed for one minute at a temperature of 60° C., SYBR green (Applied Biosystem) was used as a fluorescent material, and 7300 Real-time PCR manufactured by Applied Biosystem Company was used. The reactions other than the annealing were performed by using a method known in the art according to a protocol provided by the manufacturer. For the control, mRNA transcribed from a beta actin gene was used, and measurement results were indicated by dividing an amount of mRNA of fibronectin quantified from the RT-PCT results by an amount of mRNA of beta actin. As a result, due to the administration of streptozotocin, an expression level of fibronectin of the renal cortex was increased 1.4±0.1 times greater than that of the control, and due to the administration of (R)-carbamic acid 3-[4-(3,4-dimethoxy-phenyl)-piperazine-1-yl]-3-oxo-1-phenyl-propyl ester, an expression level of fibronectin of the renal cortex was decreased 1.2±0.1 times smaller than that of the control. From the results, it was confirmed that the compound was effective for inhibiting renal fibrosis induced by diabetes.

EXAMPLE 14

Pharmaceutical Effect Test on Inflammatory Reaction in Animal Model Having Induced Diabetic Nephropathy When diabetic nephropathy is induced by streptozotocin, inflammatory reactions are increased in the kidney and thus, expression of various inflammation related genes (for example, PAI-1, MCP-1, and TGF-131) is increased. Accordingly, in order to confirm a pharmaceutical effect of the compound on inflammation reactions, an amount of mRNA transcribed from PAI-1, MCP-1, and TGF-β1 genes was measured from the renal cortex tissues of the respective groups used in Example 13 by the RT-PCR used in Example 13 (see FIGS. 4, 5, and 6). The genes were amplified using the following primer sequences: a forward primer (5'-TCCGC-CATCACCATTTT-3'; SEQ ID NO: 3) and a reverse primer (5'-GTCAGTCATGCCCAGCTTCTC-3'; SEQ ID NO: 4) which were used to amplify PAI-1; a forward primer (5'-CCTCCACCACTATGCAGGTCTCC-3'; SEQ ID NO: 5) and a reverse primer (5'-GCACGTGGATGCTACAGGC-3'; SEQ ID NO: 6) which were used to amplify MCP-1; and a forward primer (5'-CCAACTACTGCTTCAGCTCCA-3'; SEQ ID NO: 7) and a reverse primer (5'-GTCTCCAGGCTC-CAAATGT-3'; SEQ ID NO: 8) which were used to amplify TGF-β1.

Figure 4:
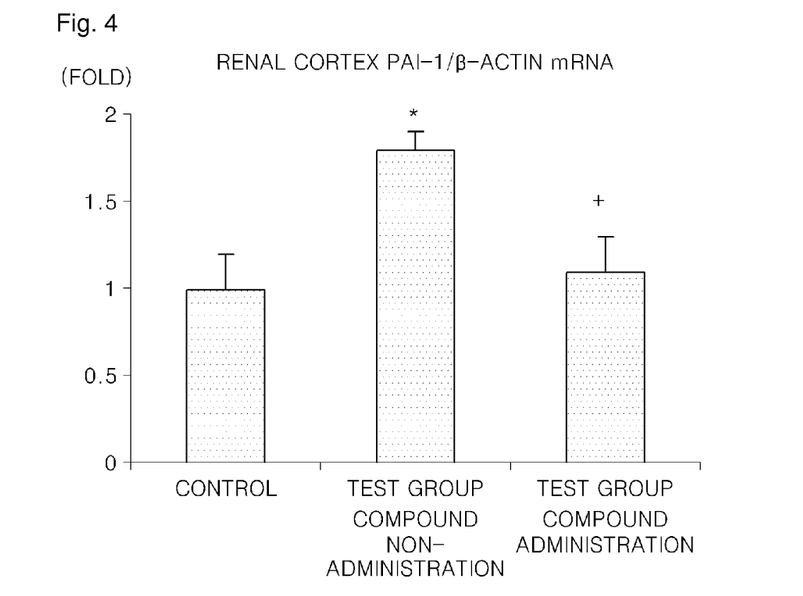
FIG. 4 shows measurement results of an amount of mRNA transcribed from a PAI-1 gene in renal cortex tissues after a compound according to an embodiment of the present invention was administered to diabetes-induced mice.
Figure 5:
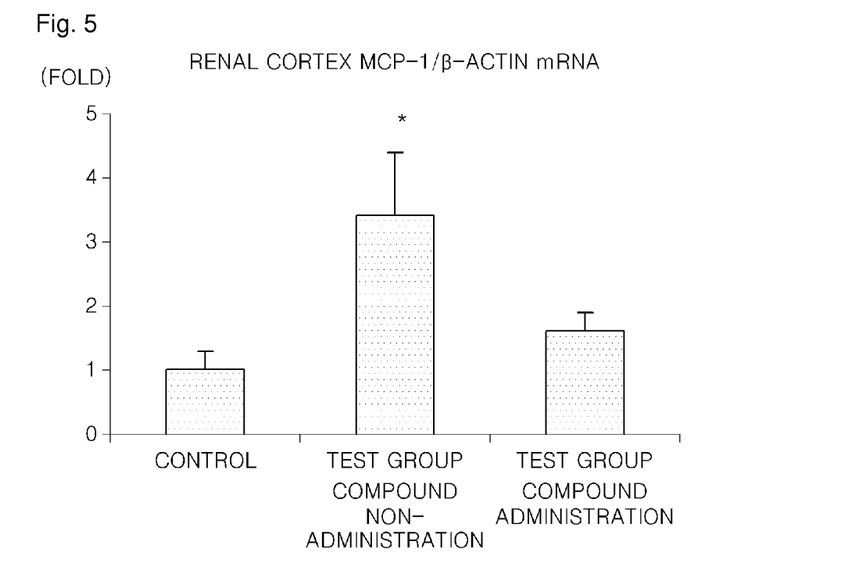
FIG. 5 shows measurement results of an amount of mRNA transcribed from a MCP1 gene in renal cortex tissues after a compound according to an embodiment of the present invention was administered to diabetes-induced mice.
Figure 6:
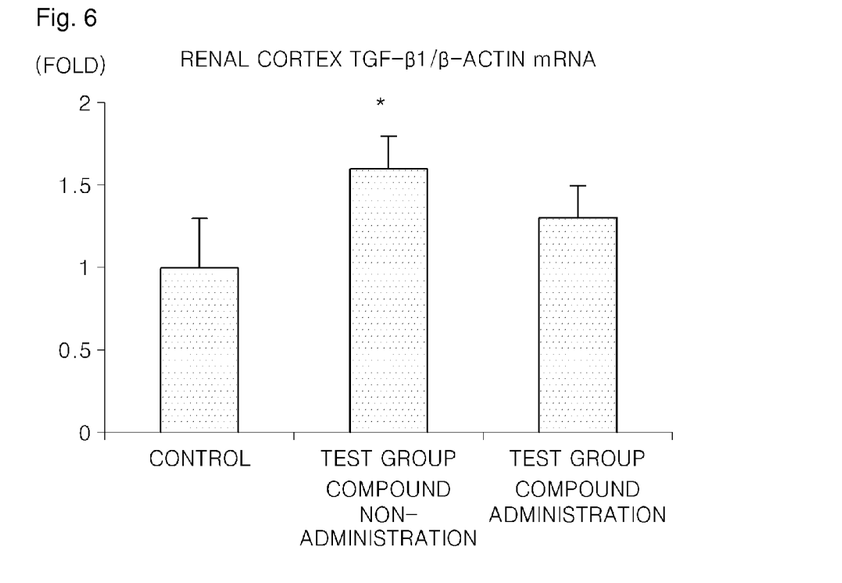
FIG. 6 shows measurement results of an amount of mRNA transcribed from a TGF β1 gene in renal cortex tissues after a compound according to an embodiment of the present invention was administered to diabetes-induced mice, wherein in FIGS. 1 to 6, * indicates that there is a statistical significance between a control and a test group to which a compound was not administered, and + indicates that there is a statistical significance between a test group to which a compound was not administered and a test group to which a compound was administered.

As a result, expressions of PAI-1, MCP-1 and TGF-β1, which are inflammation related genes, in the renal cortex were respectively increased 1.8±0.1, 3.4±1.0, and 1.6±0.2 times greater than that of the control, and due to the administration of (R)-carbamic acid 3-[4-(3,4-dimethoxy-phenyl)-piperazine-1-yl]-3-oxo-1-phenyl-propyl ester, expression levels of PAI-1, MCP-1 and TGF-β1 genes in the renal cortex were respectively decreased 1.1±0.2, 1.6±0.3 and 1.3±0.2 times smaller than the control. From this result, it was confirmed that the compound was effective for inhibiting expression of inflammation-related genes induced by diabetes.

From the results of Examples 13 and 14, it was confirmed that since the compound inhibits expression of fibrosis and inflammation-related genes causing diabetic nephropathy, the compound is useful in preventing or treating diabetic nephropathy.

EXAMPLE 15

Administration of (R)-carbamic acid 3-[4-(3,4-dimethoxy-phenyl)-piperazine-1-yl]-3-oxo-1-phenyl-propyl ester and preparation of table including the same (expectation)

The compound according to the present invention is used in preventing or treating diabetic nephropathy, diabetic neuropathy, diabetic vascular complications, hyperlipidemia, coronary artery disease, or inflammation. A clinically appropriate administration amount (oral administration) was 300 mg per adult.

Based on the administration amount, a tablet containing components shown in Table 2 below was prepared by using a conventional method. Avicel 102 (microcrystal cellulose) was used as an excipient.

Table 2

TABLE 2

| Component | Amount |
|---|---|
| (S)-carbamic acid 3-[4-(3,4-dimethoxy-phenyl)-piperazine-1-yl]-3-oxo-1-phenyl-propyl ester | 300 mg |
| Povidon K30 | 50 mg |
| Microcrystal cellulose | 170 mg |
| Sodium starch glycorate | 27.5 mg |
| Magnesium starate | 2.5 mg |
| Total | 550 mg |

An appropriate administration amount of the compound was 60 kg per adult, which is equivalent to one or two tablets containing the compound.

When the pharmaceutical compositions according to the present invention are used, diabetic nephropathy, diabetic neuropathy, diabetic vascular complications, hyperlipidemia, coronary artery disease, or inflammation may be effectively prevented or treated.

While the present invention has been particularly shown and described with reference to exemplary embodiments thereof, it will be understood by those of ordinary skill in the art that various changes in form and details may be made therein without departing from the spirit and scope of the present invention as defined by the following claims.

Sequence Listing Free Text

The sequences of the nucleotide or polypeptide of SEQ ID NO: 1 through SEQ ID NO: 8 are filed as the Sequence Listing, and contexts in the Sequence Listing are incorporated into this application in their entities.

This application contains references to amino acid sequences and/or nucleic acid sequences which have been submitted herewith as the sequence listing text file. The aforementioned sequence listing is hereby incorporated by reference in its entirety pursuant to 37 C.F.R. §1.52(e).

The invention claimed is:

1. A method for treating a diabetic complication, comprising administering to a subject in need of treatment a therapeutically effective amount of a compound selected from the group consisting of:

carbamic acid 3-[4-(3,4-dimethoxy-phenyl)-piperazine-1-yl]-3-oxo-1-phenyl-propyl ester;

carbamic acid 3-[4-(3,4-dimethoxy-phenyl)-piperazine-1-yl]-1-(4-fluoro-phenyl)-3-oxo-propyl ester;

carbamic acid 3-(4-benzo[1,3]dioxol-5-yl-piperazine-1-yl)-3-oxo-1-phenyl-propyl ester;

carbamic acid 3-[4-(3,4-dimethoxy-phenyl)-piperazine-1-yl]-1-(4-trifluoromethyl-phenyl)-3-oxo-propyl ester;

carbamic acid 3-[4-(3,4-dimethoxy-phenyl)-piperazine-1-yl]-1-(4-nitro-phenyl)-3-oxo-propyl ester;

(R)-carbamic acid 3-[4-(4-chloro-phenyl)-piperazine-1-yl]-3-oxo-1-phenyl-propyl ester;

(S)-carbamic acid 3-[4-(3,4-dimethoxy-phenyl)-piperazine-1-yl]-3-oxo-1-phenyl-propyl ester;

(R)-carbamic acid 3-[4-(3,4-dimethoxy-phenyl)-piperazine-1-yl]-3-oxo-1-phenyl-propyl ester;

carbamic acid 3-[4-(3,4-dimethoxy-phenyl)-piperazine-1-yl]-1-phenyl-butyl ester; and carbamic acid 3-[4-(3,4-dimethoxy-phenyl)-piperazine-1-yl]-1-(4-chloro-phenyl)-3-oxo-propyl ester, or a pharmaceutically acceptable salt, isomer, solvate, or hydrate thereof, wherein the diabetic complication is selected from the group consisting of diabetic nephropathy, diabetic neuropathy, a diabetic vascular complication and diabetic inflammation.

2. The method of claim 1, wherein the diabetic complication is caused by enhanced expression of 15-lipoxygenase.

3. The method of claim 1, wherein the method further comprises a step of identifying a subject in need of the treatment before the administering step.

4. The method of claim 1, wherein the compound is administered as a pharmaceutical composition comprising a pharmaceutically acceptable carrier.

5. The method of claim 4, wherein the pharmaceutically acceptable carrier is microcrystal cellulose.

6. The method of claim 1, wherein the compound is orally administered.

7. The method of claim 1, wherein the pharmaceutically effective amount is about 300 mg.

8. The method of claim 1, wherein the compound is
carbamic acid 3-[4-(3,4-dimethoxy-phenyl)-piperazine-1-yl]-3-oxo-1-phenyl-propyl ester;
(S)-carbamic acid 3-[4-(3,4-dimethoxy-phenyl)-piperazine-1-yl]-3-oxo-1-phenyl-propyl ester; or
(R)-carbamic acid 3-[4-(3,4-dimethoxy-phenyl)-piperazine-1-yl]-3-oxo-1-phenyl-propyl ester.

9. The method of claim 8, wherein the compound is (R)-carbamic acid 3-[4-(3,4-dimethoxy-phenyl)-piperazine-1-yl]-3-oxo-1-phenyl-propyl ester.

10. The method of claim 1, wherein the disease is diabetic neuropathy.

* * * * *

```
SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Forward primer for amplifying fibronectin gene

<400> SEQUENCE: 1
gccacaccta caaccagtat                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for amplifying fibronectin gene

<400> SEQUENCE: 2
atgaccactc agaaatggag                                              20

<210> SEQ ID NO 3
<211> LENGTH: 17
<212> TYPE: DNA
<213> ORGANISM: Artificial Sequence
<220> FEATURE:
```

```
<223> OTHER INFORMATION: Forward primer for amplifying PAI-1 gene

<400> SEQUENCE: 3
tccgccatca ccatttt                                                  17

<210> SEQ ID NO 4
<211> LENGTH: 21
<212> TYPE: DNA
<213> ORGANISM: Artificial Sequence
<220> FEATURE:
<223> OTHER INFORMATION: Reverse primer for amplifying PAI-1 gene

<400> SEQUENCE: 4
gtcagtcatg cccagcttct c                                             21

<210> SEQ ID NO 5
<211> LENGTH: 23
<212> TYPE: DNA
<213> ORGANISM: Artificial Sequence
<220> FEATURE:
<223> OTHER INFORMATION: Forward primer for amplifying MCP-1 gene

<400> SEQUENCE: 5
cctccaccac tatgcaggtc tcc                                           23

<210> SEQ ID NO 6
<211> LENGTH: 19
<212> TYPE: DNA
<213> ORGANISM: Artificial Sequence
<220> FEATURE:
<223> OTHER INFORMATION: Reverse primer for amplifying MCP-1 gene

<400> SEQUENCE: 6
gcacgtggat gctacaggc                                                19

<210> SEQ ID NO 7
<211> LENGTH: 21
<212> TYPE: DNA
<213> ORGANISM: Artificial Sequence
<220> FEATURE:
<223> OTHER INFORMATION: Forward primer for amplifying TGF-beta 1 gene

<400> SEQUENCE: 7
ccaactactg cttcagctcc a                                             21

<210> SEQ ID NO 8
<211> LENGTH: 19
<212> TYPE: DNA
<213> ORGANISM: Artificial Sequence
<220> FEATURE:
<223> OTHER INFORMATION: Reverse primer for amplifying TGF-beta 1 gene

<400> SEQUENCE: 8
gtctccaggc tccaaatgt                                                19
```